(12) United States Patent
Terry et al.

(10) Patent No.: US 12,175,556 B2
(45) Date of Patent: Dec. 24, 2024

(54) OPTICAL AXIS CALIBRATION OF ROBOTIC CAMERA SYSTEM

(71) Applicant: Alcon Inc., Fribourg (CH)

(72) Inventors: Patrick Terry, Goleta, CA (US); Ashok Burton Tripathi, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 378 days.

(21) Appl. No.: 17/659,123

(22) Filed: Apr. 13, 2022

(65) Prior Publication Data

US 2022/0392012 A1 Dec. 8, 2022

Related U.S. Application Data

(60) Provisional application No. 63/197,644, filed on Jun. 7, 2021.

(51) Int. Cl.
*G06T 1/00* (2006.01)
*G06T 7/80* (2017.01)

(52) U.S. Cl.
CPC .............. *G06T 1/0014* (2013.01); *G06T 7/80* (2017.01); *G05B 2219/39008* (2013.01); *G05B 2219/39045* (2013.01); *G06T 2207/30208* (2013.01)

(58) Field of Classification Search
CPC ............. G06T 1/0014; G06T 7/80; G06T 2207/30208; G06T 2207/10028;
(Continued)

(56) References Cited

U.S. PATENT DOCUMENTS

| 2013/0010081 A1* | 1/2013 | Tenney | H04N 13/20 348/47 |
| 2013/0331644 A1* | 12/2013 | Pandya | A61B 34/30 600/102 |

(Continued)

FOREIGN PATENT DOCUMENTS

| CA | 2912589 C | * | 6/2021 | ............ B21J 15/14 |
| CN | 111203880 A | * | 5/2020 | ............ B25J 19/023 |

(Continued)

OTHER PUBLICATIONS

Pose Determination of a Robot Manipulator Based on Monocular Vision—2016 (Year: 2016).*

*Primary Examiner* — Nizar N Sivji
(74) *Attorney, Agent, or Firm* — Quinn IP Law

(57) ABSTRACT

A method, instructions for which are executed from a computer-readable medium, calibrates a robotic camera system having a digital camera connected to an end-effector of a serial robot. The end-effector and camera move within a robot motion coordinate frame ("robot frame"). The method includes acquiring, using the camera, a reference image of a target object on an image plane having an optical coordinate frame, and receiving input signals, including a depth measurement and joint position signals. Separate roll and pitch offsets are determined of a target point within the reference image with respect to the robot frame while moving the robot. Offsets are also determined with respect to x, y, and z axes of the robot frame while moving the robot through another motion sequence. The offsets are stored in a transformation matrix, which is used to control the robot during subsequent operation of the camera system.

20 Claims, 5 Drawing Sheets

(58) Field of Classification Search
CPC ....... B25J 19/023; B25J 9/1692; A61B 90/20;
A61B 90/25; A61B 90/50; A61B 34/30;
A61B 2017/00725; A61B 2034/2059;
A61B 2034/2065; A61B 2090/371; A61B
3/13; G05B 2219/39008; G05B
2219/39045
See application file for complete search history.

(56) References Cited

U.S. PATENT DOCUMENTS

| | | | |
|---|---|---|---|
| 2016/0214255 A1* | 7/2016 | Uhlenbrock | B25J 9/1674 |
| 2016/0346932 A1* | 12/2016 | Deng | B25J 9/1692 |
| 2018/0161983 A1* | 6/2018 | Yamaguchi | B25J 19/023 |
| 2019/0047152 A1* | 2/2019 | Tonogai | B25J 9/1697 |
| 2020/0282575 A1 | 9/2020 | Haeusler et al. | |
| 2020/0289223 A1* | 9/2020 | Denlinger | A61B 34/77 |
| 2021/0225032 A1* | 7/2021 | Hain | G06T 7/73 |
| 2022/0172399 A1* | 6/2022 | Islam | G06T 5/80 |

FOREIGN PATENT DOCUMENTS

| | | | |
|---|---|---|---|
| CN | 111445533 A | 7/2020 | |
| WO | WO-2020143918 A1 * | 7/2020 | B25J 9/0093 |

\* cited by examiner

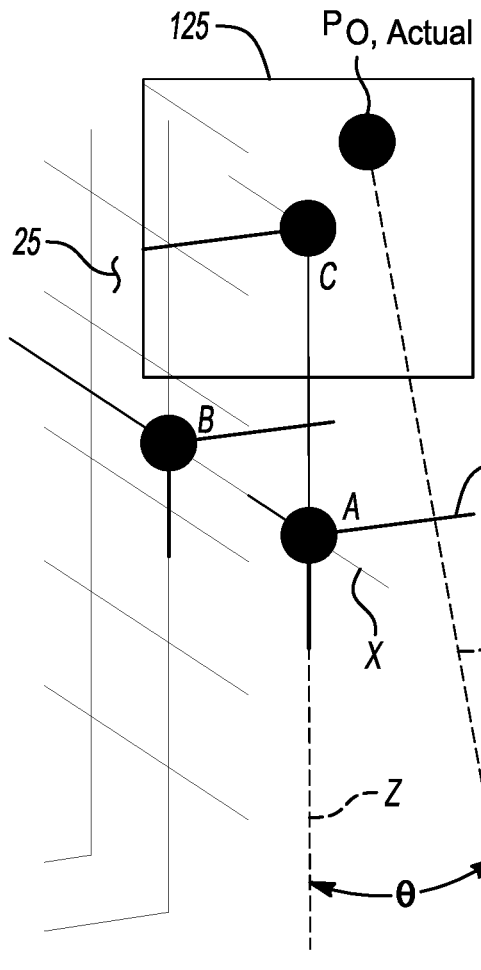
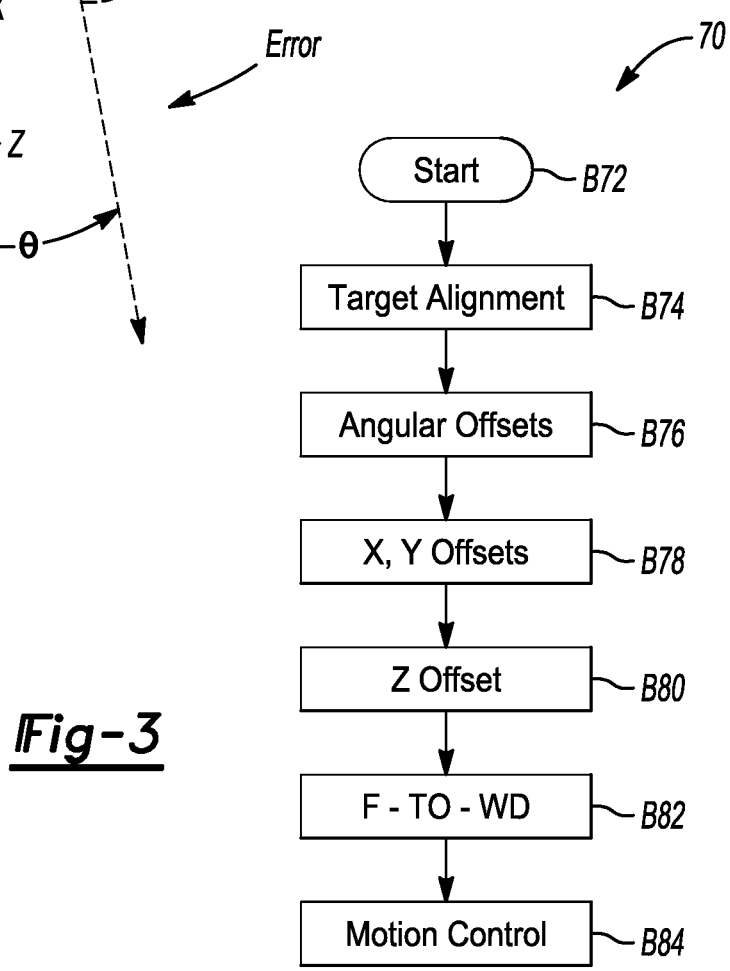
Fig-2
Fig-3

OPTICAL AXIS CALIBRATION OF ROBOTIC CAMERA SYSTEM

CROSS-REFERENCE TO RELATED APPLICATIONS

This application claims priority to, and benefit of, U.S. Provisional Patent Application Ser. No. 63/197,644, filed on Jun. 7, 2021, which is hereby incorporated by reference in its entirety.

TECHNICAL FIELD

The present disclosure relates to automated methodologies and systems for calibrating an optical axis of a robotic camera system.

BACKGROUND

Surgeons are often assisted by real-time digital imaging of a patient's target anatomy. An ophthalmologist performing vitreoretinal surgery, for instance, views highly magnified images of a retina or other intraocular anatomy in real time using high-resolution medical display screens positioned within easy view of the surgeon, or through optical pieces of a microscope. The camera may be securely mounted to an end-effector disposed at a distal end of an articulated serial robot. The collective motion of the various joints and interconnected linkages of the serial robot is controlled via an electronic control unit in order to properly orient and position the camera with respect to the target anatomy.

To this end, a multi-axis serial robot having multiple interconnected arm segments may be used in a surgical suite to enable the connected digital camera to rotate and translate as needed. An example of such a serial robot is disclosed in U.S. Pat. No. 10,917,543B2 to Alcon, Inc., titled "Stereoscopic Visualization Camera and Integrated Robotics Platform", which is hereby incorporated by reference in its entirety. Robotic motion occurs within a robot motion coordinate frame of reference ("robot frame"), with the robot frame having at least the nominal x, y, and z axes of a typical Cartesian coordinate frame.

Robotic camera systems used to assist in the performance of an automated machine vision-assisted tasks are defined by operating parameters, including a required minimum resolution, field-of-view, depth-of field, and optical working distance. Optical working distance in particular as used herein describes the linear distance along an optical axis extending between a Center of Projection (CoP) of the digital camera and an imaged target located in an image plane, as opposed to the distance between a bottom of the camera or its housing and the target, e.g., a patient. The digital camera, which as noted above is coupled to a distal end of the serial robot via a suitable end-effector, digitally images the target within the camera's own optical coordinate frame of reference ("camera frame"). The camera frame in most mathematical models of the types commonly used to control serial robot motion assumed to be arranged orthogonally to the robot frame. Thus, the various electronic motion control commands and feedback signals used to position the end-effector and digital camera within a workspace must first be translated into the robot frame in order to ensure that the digital camera remains properly focused on an intended target point relative to the robot's understanding of its own relative position within the robot frame.

SUMMARY

Disclosed herein are automated methods and accompanying systems for calibrating the optical axis of a digital camera within a robotic camera system. The method proceeds without foreknowledge or modeling of relevant parameters of the camera's optics. Instead, the method results in generation, using the parameters, of a homogenous transformation matrix that is then employed in subsequent control of the robotic camera system in accordance with the present teachings.

As understood in the art, machine vision applications requiring relatively low levels of position precision tend to ignore the potential differences between the different robot and camera coordinate frames. In contrast, machine vision applications requiring relatively high levels of positional accuracy, such as precision microsurgeries, may attempt to fully model the behavior of the optical system, and to thereafter map the resulting optical model to a kinematic model of the robot's motion behavior. However, implementation of such an approach presents an onerous programming task, one fraught with potential position error due to the extreme difficulty in deriving an accurate and dependable optical model.

Applications forgoing reliance on the availability of a full optical model can therefore experience high levels of position error when calculating a position of a target point of interest on a reference image. This problem is exacerbated in precision applications having high optical distances. Relatively large position errors can result under such conditions when the camera's view vector is rotated or skewed by even a small amount. For example, an ophthalmic microscope may have a fixed or variable optical distance on the order of 250 mm-350 mm. In such an exemplary configuration, an optical axis skew angle of just 0.1 degrees may result in as much as 5 mm-10 mm of position error on the image plane.

As an illustration of the possible practical effect of such position error, one may consider the example case of an eye surgeon expecting to view a particular target point of interest on a displayed optical image, e.g., dead center of a dilated pupil during cataracts surgery. Due to the noted position error, however, the surgeon would instead view an entirely different target point, perhaps one located on the surface of the surrounding iris. The surgeon would then require further control adjustments in order to properly locate the desired target point, thereby extending surgery time and producing suboptimal results.

To that end, the method described in detail herein enables a simplified automated calibration process to be implemented upon connection of a digital camera to a robot end-effector. Such a connection does not always result in perfect alignment of the camera's optical coordinate frame ("camera frame") relative to the robot's motion coordinate frame ("robot frame"), as expected by the robot's underlying target acquisition and tracking logic, itself referred to herein as a lock-to-target or LTT function. That is, the camera's view vector could be slightly skewed due to surgeon-based adjustments, or due to imperfections in the mechanical coupling mechanism used to secure the camera to the end-effector of the serial robot. This in turn can lead to unacceptably high levels of position error, particularly in applications utilizing greater optical distances. In order minimize resulting position error, a transformation matrix is generated during a calibration stage of the method, with subsequent motion control stages of the robotic camera system controlled using the generated transformation matrix.

More specifically, the robotic camera system contemplated herein includes a digital camera coupled to the end-effector, with the end-effector being disposed at a distal end of the serial robot. The end-effector and the connected digital camera thus move within the robot frame by operation of the serial robot. In general, the method proceeds by acquiring reference images of a target object, e.g., a surface of a patient's eye or another target anatomy in a non-limiting eye surgery use case. The images are collected within the camera frame as opposed to the above-noted robot frame.

The method also includes receiving input signals via an electronic control unit (ECU) in wired or wireless communication with the serial robot, with the ECU configured with a model of the robot's kinematics. The ECU is characterized by an absence of a model of the camera optics, as noted above. The input signals include a depth measurement indicative of a linear distance to the target object/image plane, and joint position signals indicative of a position of the end-effector within the robot frame. For clarity, the robot frame may be described as having the nominal x-axis, a y-axis, and a z-axis of a typical Cartesian frame of reference.

The method may include determining, via the ECU, a roll angle offset and a pitch angle offset as angular offsets, with such offsets taken relative to the robot frame, of a target point located in the reference image(s). The method also includes determining separate x-axis, y-axis, and z-axis offsets of the target point, and thereafter recording or storing the roll, pitch, x-axis, y-axis, and z-axis offsets in a homogenous transformation matrix within memory of or accessible by the ECU. The transformation matrix is then used by the ECU, along with the aforementioned robotic kinematics, to control a motion sequence of the serial robot during subsequent operation of the robotic camera system. Thus, once the digital camera has been properly calibrated in accordance with the method, the robotic camera system need not be recalibrated with each subsequent use, provided that the camera remains connected to the end-effector.

The camera in some configurations may have a variable optical distance, e.g., to enable the surgeon to vary the same during surgery. The variable optical distance may be adjusted via a focus motor. In such an embodiment, the method may include recording a plurality of z-axis offsets in a lookup table while adjusting the variable optical distance through an optical distance or focal range via the focus motor. Determining the z-axis offset in such an embodiment may include extracting the z-axis offset from the pre-populated lookup table during the subsequent motion sequence.

The method may optionally include processing an autofocus setting of the camera system via the ECU to determine the above-noted depth measurement. Alternatively, the ECU may measure the depth measurement using a depth sensor, e.g., a laser distance meter or an optical sensor.

Acquiring the reference images of the target object within the optical frame may include collecting digital images of a two-dimensional checkerboard graphic or another pixelated target using the digital camera.

The serial robot may be optionally embodied as a six-axis ophthalmic surgical robot, with the digital camera connected to or integral with an ophthalmic microscope coupled to an end-effector of such a robot. Subsequent operation of the robotic camera system may include performing three-dimensional visualization of a target eye during an eye surgery, for instance during vitrectomy or lens replacement/cataracts surgery.

Another aspect of the disclosure includes a camera system having a digital camera and an ECU in communication therewith. The digital camera, e.g., a stereoscopic camera, connected to or integral with a microscope, is connectable to an end-effector of a serial robot. The end-effector and the digital camera move within the robot motion frame. The ECU, which is in communication with the digital camera, is configured to perform the method as summarized above.

A computer-readable medium is also disclosed herein, on which is recorded instructions. Execution of the instructions by a processor, for instance of the above-noted ECU, causes the processor, when used with a robot camera system having a digital camera connected to an end-effector of a serial robot, to perform the method as summarized above.

The foregoing summary is not intended to represent every possible embodiment or aspect of the subject disclosure. Rather, the summary is intended to exemplify some of the novel aspects and features disclosed herein. The above-noted and other possible features and advantages of the subject disclosure will be readily apparent from the following detailed description of representative embodiments and modes for carrying out the subject disclosure when taken in connection with the accompanying drawings and the appended claims.

BRIEF DESCRIPTION OF THE DRAWINGS

FIG. 2 is a schematic depiction of position errors that may result from slight angular skew of an optical axis or view vector within the robotic camera system of FIG. 1.

FIG. 3 is a flow chart describing an exemplary embodiment of a method for calibrating the optical axis of the robotic camera system shown in FIG. 1.

Figure 1:
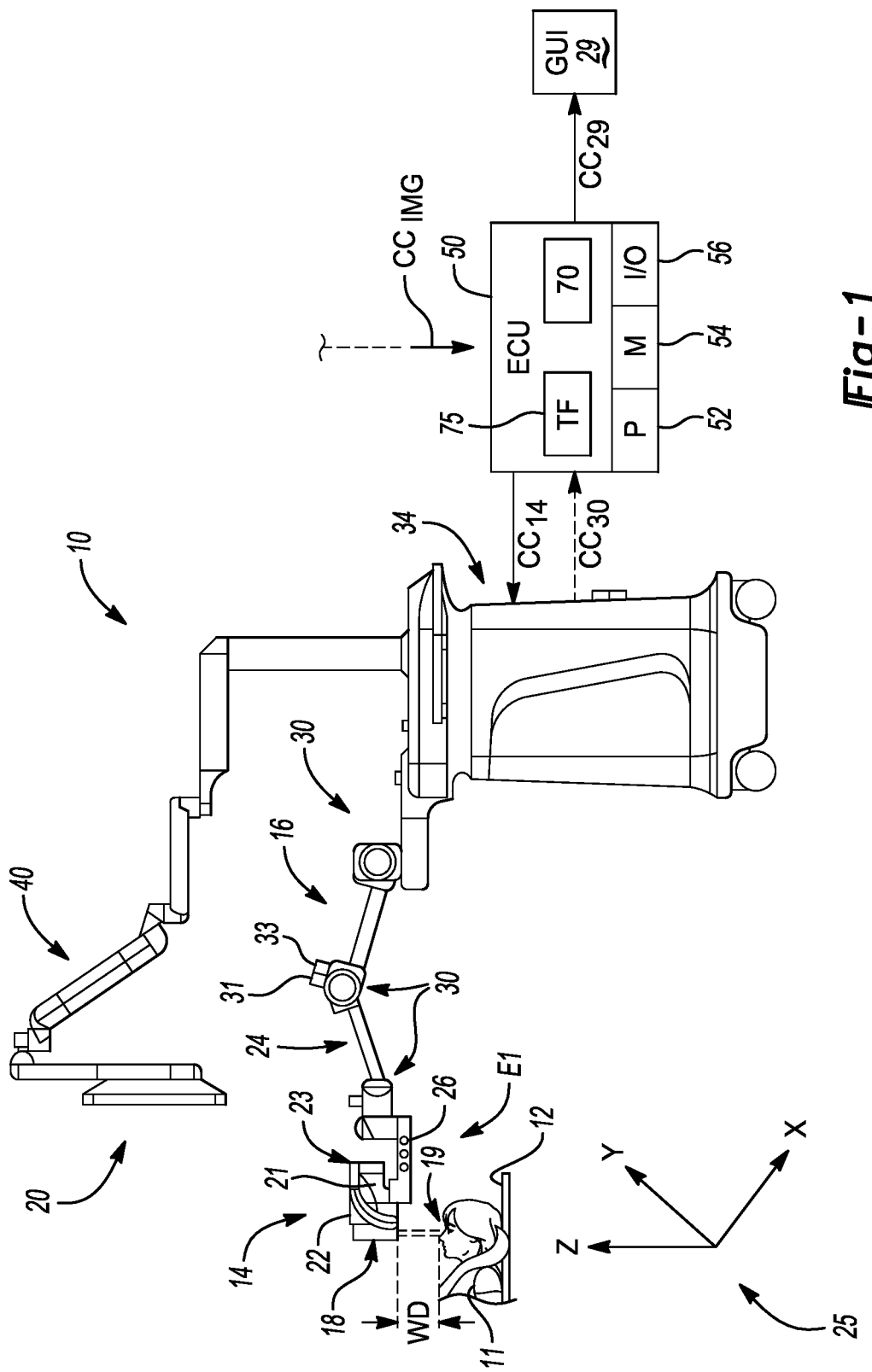
FIG. 1 illustrates a diagram of a robotic camera system in which a digital camera is connected to an end-effector of a serial robot, with the optical axis of the digital camera being calibratable in accordance with the present disclosure.

The foregoing and other features of the present disclosure are more fully apparent from the following description and appended claims, taken in conjunction with the accompanying drawings.

DETAILED DESCRIPTION

Embodiments of the present disclosure are described herein. It is to be understood, however, that the disclosed embodiments are merely examples and other embodiments can take various and alternative forms. The figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure.

As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Referring to the drawings, wherein like reference numbers refer to like components, a surgical suite 10 is depicted in FIG. 1 as it might appear during a representative eye surgery, with a patient 11 resting on a surgical table 12. The surgical suite 10 as contemplated herein is equipped with a robotic camera system 14, which itself is inclusive of an articulated serial robot 16 and a digital camera 18. Within the scope of the present disclosure, the robotic camera system 14 is controlled by operation of an electronic control unit (ECU) 50, which in turn is programmed in software and equipped in hardware, i.e., configured, to execute computer-readable instructions embodying a calibration method 70, an example of which is described below with particular reference to FIG. 3. Execution of the method 70 enables simplified and expedited calibration of the robotic camera system 14 in the manner set forth below.

The robotic camera system 14 enables a user, in this non-limiting exemplary instance a surgeon (not shown), to view magnified images of a target object 19 under high magnification, with high-definition visualization facilitated by display of the images on one or more high-resolution display screens 20. To that end, the method 70 described in detail hereinbelow enables a simplified automated calibration process to be implemented by the ECU 50 upon connection of the digital camera 18 to a robot end-effector 26 disposed at a distal end E1 of the serial robot 16, e.g., a mounting plate, bracket, clamp, or other suitable attachment hardware.

The connection of the digital camera 18 to the end-effector 26 does not always result in a perfect orthogonal or other intended alignment of the camera's optical axis and corresponding view vector with the robot's motion coordinate frame 25, hereinafter referred to as the robot frame 25 for simplicity, as represented in FIG. 1 as nominal x, y, and z axes of a typical Cartesian reference frame. That is, the view vector of the digital camera 18 along its optical axis may be slightly skewed due to surgeon-based view vector adjustments, camera-specific lens variations, or alignment errors due to installation.

Applications utilizing an extended optical working distance (WD) between the digital camera 18 and the target object 19 can ultimately lead to unacceptably high levels of position error. To minimize such position error, the ECU 50 generates a transformation matrix (TF) 75 during a calibration stage of the robotic camera system 14, and then controls subsequent motion of the robotic camera system 14 using the transformation matrix 75. Such a transformation matrix 75 is derived without foreknowledge or modeling of relevant parameters of the camera's optics. The corrected position is then employed by the ECU 50, along or in conjunction with distributed motor control processors, when subsequently controlling motion of the serial robot 16 when imaging the target object 19 during a subsequent operation of the robotic camera system 14.

As appreciated in the art, the digital camera 18 includes therein a set of optical image sensors (not shown) that are collectively configured to acquire and/or record incident light when forming a pixel image. Such image sensors in a possible stereoscopic embodiment include separate right-side and left-side optical image sensors for right and left optical paths, respectively, and may include complementary metal-oxide-semiconductor ("CMOS") sensing elements, N-type metal-oxide-semiconductor ("NMOS"), semiconductor charge-coupled device ("CCD") sensing elements, or various other application-suitable devices.

The digital camera 18 may be located or within in an adjustable head unit 22 and configured to collect digital image data (arrow $CC_{IMG}$) of the target object 19, which may be processed and filtered by the ECU 50 to generate live stereoscopic views of the target object 19. A selector knob 23 may be mounted on or to the head unit 22 to enable a user to adjust specific features of the digital camera 18, such as the level magnification or degree of focus, as well as to enable the user to manually position the head unit 22.

The digital camera 18 is configured to acquire two-dimensional or three-dimensional images of the target object 19 in real-time for presentation in different forms, including but not limited to captured still images, real-time images, and/or digital video signals. "Real-time" as used herein refers to the updating of information at the same or similar rate at which data is acquired. More specifically, "real-time" means that the image data is acquired, processed, and transmitted at a sufficiently high data transfer rate and with sufficiently low delay such that, when images constructed from the image data (arrow $CC_{IMG}$) is ultimately displayed on the display screen(s) 20, the displayed images appear to move smoothly, i.e., without user-noticeable judder or latency. For reference, a suitable representative data transfer rate is 30-frames per second (30-fps) or more, displayed at about 60-fps, with no more than about $\frac{1}{30}^{th}$ of a second of delay.

The digital camera 18 whose optical axis is calibrated in accordance with the disclosure includes a lens assembly (not shown) having the noted optical working distance (WD). When the optical working distance (WD) is variable within a set range, the focus motor 21 selectively moves one or more lenses of the lens assembly in order to adjust the working distance, which as understood in the art is the linear distance between the digital camera 18 to a reference plane within which the target object 19 is in focus. In some embodiments, the optical working distance (WD) is adjustable by moving a rear working distance lens via the focus motor 21 relative to a front working distance lens, with "front" and "rear" referring to relative position respectively closer to and farther from the target object 19. The focus motor 21 may be variously embodied as an electric motor or another suitable rotary actuator, or as a linear actuator such as a stepper motor, a shape memory alloy actuator, or another application-suitable actuator.

Still referring to FIG. 1, the serial robot 16 includes an articulated robot arm 24 that is operatively connected to and configured to selectively move the head unit 22, which in turn is mechanically coupled to the end-effector 26. An operator may position and orient the digital camera 18 via automated position control of the robot arm 24. The robot arm 24 as represented in FIG. 1 includes multiple revolute joints 30 collectively configured to provide, in a representative embodiment, six degrees of freedom ("6-DoF") when positioning and/or orienting the head unit 22.

Sensory data from the force sensor(s) may be employed by the ECU 50 to determine the angular position and adjustment speeds of the various joints 30 when assisting movement of the digital camera 18. Each respective joint 30 may be equipped with one or more corresponding joint motors 31 and a respective joint position sensor 33. Each joint motor 31 in turn is configured to rotate a corresponding one of the revolute joints 30 around a respective axis within the robot frame 25 while the joint position sensors 33 transmit a measured angular position of each of the respective joints 30 to the ECU 50.

The robot arm 24 is selectively operable to extend a viewing range of the digital camera 18 along the x, y, and/or z axis of the robot frame 25. For instance, the robot arm 24 and the digital camera 18 coupled thereto may be connected to a mobile cart 34, which in turn may be physically or remotely connected to the display screen(s) 20 via an adjustable arm 40. The cart 34 may be constructed of lightweight and easily sanitized medical grade materials, e.g., painted aluminum or stainless steel, and possibly used to house the ECU 50 for the purpose of protecting its constituent hardware from possible ingress of dust, debris, and moisture. Although the display screen 20 supported by the adjustable arm 40 is depicted in FIG. 1 in the form of a high-resolution/4K or higher medical grade monitor, other embodiments may include, e.g., a wall-mounted high- or ultra-high definition television, smart eyewear or another wearable monitor, a projector, or a computer screen, without limitation.

The digital image data (arrow $CC_{IMG}$) of the target object 19 as collected by operation of the digital camera 18 is communicated to the ECU 50 wirelessly or over physical high-speed transfer conductors. The ECU 50 in turn performs the requisite digital image processing steps needed to constitute and display high-resolution digital images. For example, the ECU 50 may combine or interleave video signals from the digital camera 18 to create a stereoscopic image. The ECU 50 may be configured to store video and/or stereoscopic video signals into a video file in an associated computer-readable medium, schematically represented in FIG. 1 as memory (M) 54.

Further with respect to the ECU 50, this computer device is depicted schematically in FIG. 1 as a unitary box solely for illustrative clarity and simplicity. Actual implemented embodiments of the ECU 50 may include one or more networked computer devices each with one or more corresponding processors (P) 52 and sufficient amounts of the above-noted memory 54, including a non-transitory (e.g., tangible) medium on which is recorded or stored a set of computer-readable instructions readable and executable by the processor(s) 52. The memory 54 may take many forms, including but not limited to non-volatile media and volatile media. Instructions embodying the method 70 of FIG. 3 may be stored in memory 54 and selectively executed by the processor(s) 52 to perform the various calibration functions described below.

As will be appreciated by those skilled in the art, non-volatile media may include optical and/or magnetic disks or other persistent memory, while volatile media may include dynamic random-access memory (DRAM), static RAM (SRAM), etc., any or all which may constitute main memory of the ECU 50. Input/output ("I/O") circuitry 56 may be used to facilitate connection to and communication with various peripheral devices inclusive of the digital camera 18,
lighting sources (not shown), and the high-resolution display screen(s) 20. A graphical user interface (GUI) 29 may be connected to the ECU 50 to enable a surgeon or clinician to enter control commands (arrow $CC_{14}$) to move the serial robot 16, and to receive measured joint angle signals (arrow CC30) indicative of the position of the serial robot 16 in free space, as well as to control operation of the digital camera 18 and otherwise interface with the ECU 50 and its various functions. Other hardware not depicted but commonly used in the art may be included as part of the ECU 50, including but not limited to a local oscillator or high-speed clock, signal buffers, filters, amplifiers, etc.

In accordance with the present disclosure, execution of the method 70 may require the ECU 50 of FIG. 1 to implement a target locking mode, referred to herein as "lock-to-target" or LTT mode, which enables the digital camera 18 to be positioned via the serial robot 16 anywhere within a defined workspace of the robot's range of motion, with LTT mode permitting changes in the optical working distance (WD) while keeping the location of the target object 19 locked in for the purpose of motion tracking, and in proper focus. As appreciated in the art, it can be difficult to maintain an image in focus when moving the serial robot 16 and changing of orientation of the digital camera 18 connected thereto, i.e., as the direction of the view vector changes. In the disclosed embodiments, therefore, the target locking mode/LTT capabilities of the ECU 50 allow the robot arm 24 to effectively operate as extension of an attending surgeon by enabling the digital camera 18 to be reoriented while remaining locked onto a specific target point.

Within this established context, the ECU 50 is programmed with computer-readable instructions embodying the method 70 of FIG. 3, which in turn is executed when calibrating the robotic camera system 14 for accurately associating motion of the serial robot 16 with resulting position changes on a pixel image of the target object 19. Execution of the method 70 ultimately results in the generation and recording of the transformation matrix 75, itself constructed as a homogenous 4×4 matrix from five parameters, i.e., N1, N2, N3, N4, N5.

According to the present strategy, parameters N1 and N2 correspond to a calculated roll offset and pitch offset, respectively, while parameters N3, N4, and N5 respectively correspond to x-axis, y-axis, and z-axis offsets. Thus, the transformation matrix 75 may be embodied as a 4×4 (sixteen-element) homogenous matrix with linear terms p=[x, y, z] and a rotational terms R=R(about x-axis)*R(about y-axis). For the purposes of the disclosed solution within an exemplary ophthalmic imaging application, yaw can be ignored. The solution otherwise proceeds without access to an analytical model of the optics of the digital camera 18. Instead, the transformation matrix 75 is applied by the ECU 50 during subsequent motion sequence of the robotic camera system 14 in order to calculate and display the true position of the target object 19 and points of interest thereon within an image plane. Thus, the corresponding pixel locations of a displayed image of the target object 19 corresponds to pixel locations in the robot frame 25.

A problem addressed by the subject disclosure when controlling the digital camera 18 with an extended optical working distance (WD) can be understood with brief reference to FIG. 2, which illustrates the robot frame 25 and the camera frame 125 of the digital camera 18 shown in FIG. 1. An origin point $P_{O, ACTUAL}$ lies in an LTT frame of reference, i.e., the camera frame 125. The z-axis of the robot frame 25 is ordinarily assumed to be the view vector 100 of the digital camera 18, which would be true absent skew of the view vector 100. Thus, FIG. 2 illustrates possible position error ("Error") relative to an original kinematics model for controlling the robotic camera system 14 of FIG. 1, which typically assumes that the view vector 100 is normal or orthogonal to the head unit 22, when in reality the view vector 100 is skewed at an angle (θ).

That is, relative to points A, B, and C in the robot frame 25, the origin point $P_{O, ACTUAL}$ may be offset a distance away from the x, y, and z axes, with possible pitch and roll offsets as well. In other words, frames 25 and 125 do not perfectly align relative to an underlying model, or stated another way, what is ordinarily assumed to be an orthogonal relationship is not exactly so. As the optical working distance (WD) increases, so too does the resulting position error. For instance, a 300 mm optical working distance and a skew angle (θ) of just 0.5 degrees could lead to a position error of 5 mm to 10 mm, with corresponding display errors in a presented image of the target object 19. The present solution therefore seeks to find angular and x-axis, y-axis, and z-axis offsets to minimize such position errors when translating the camera frame 125 to the robot frame 25 for use in subsequent motion control operations.

As appreciated in the art, LTT control functionality of the ECU 50 is performed when controlling motion of the robot arm 24 with the appended digital camera 18 shown in FIG. 1. LTT functionality enables the ECU 50 to move the robot arm 24 while keeping a starting image centered on the display screen 20. This is done by "locking" the optical working distance (WD) of FIG. 1, with the resulting moves of the digital camera 18 being spherical, with radii equal to an estimated focal length of the digital camera 18. Although such LTT functionality of the ECU 50 improves accuracy, a primary source of image error when using LTT function remains not knowing, to an acceptable level of precision, the location of the Center of Projection (CoP) and/or Focal Point (FP)-based view vector 100, and thus the location of the target object 19 in the robot frame 25 of FIG. 2.

The present teachings may be implemented as computer-executable instructions that are executed for the purpose of calibrating a robotic camera system of the type depicted in FIG. 1, i.e., one having a digital camera connected to an end-effector of a 6-DoF serial robot, with the end-effector and the digital camera moving or free to move within a robot motion coordinate frame. In general, solutions falling within the scope of the subject disclosure proceed by acquiring one or more reference images of a target object located on an image plane having an optical coordinate frame, i.e., the digital camera's coordinate frame as opposed to that of the serial robot. Input signals are received in the form of a depth measurement indicative of a linear distance between the digital camera and the target object, and a set of joint position signals collectively describing a position of the digital camera in the robot motion coordinate frame. As described above, the robot motion coordinate frame has a nominal x-axis, y-axis, and z-axis.

Suitable implementations of the method, a non-limiting exemplary embodiment of which is shown in FIG. 3 and described below, include the logical steps of determining roll and pitch offsets of a target point within the reference image, with "offset" referring to angular differences or deltas relative to the robot motion coordinate frame. Such offsets are determined while moving the serial robot through a first calibrated motion sequence, after which the method determines each of an x-axis offset, a y-axis offset, and a z-axis offset of the target point with respect to the robot motion coordinate frame. This occurs while moving the serial robot through a second calibrated motion sequence. The method proceeds from here by storing the angular and linear/axial offsets in a transformation matrix, with the transformation matrix later used to control a third motion sequence of the serial robot, i.e., during subsequent operation of the robotic camera system.

Figure 4:
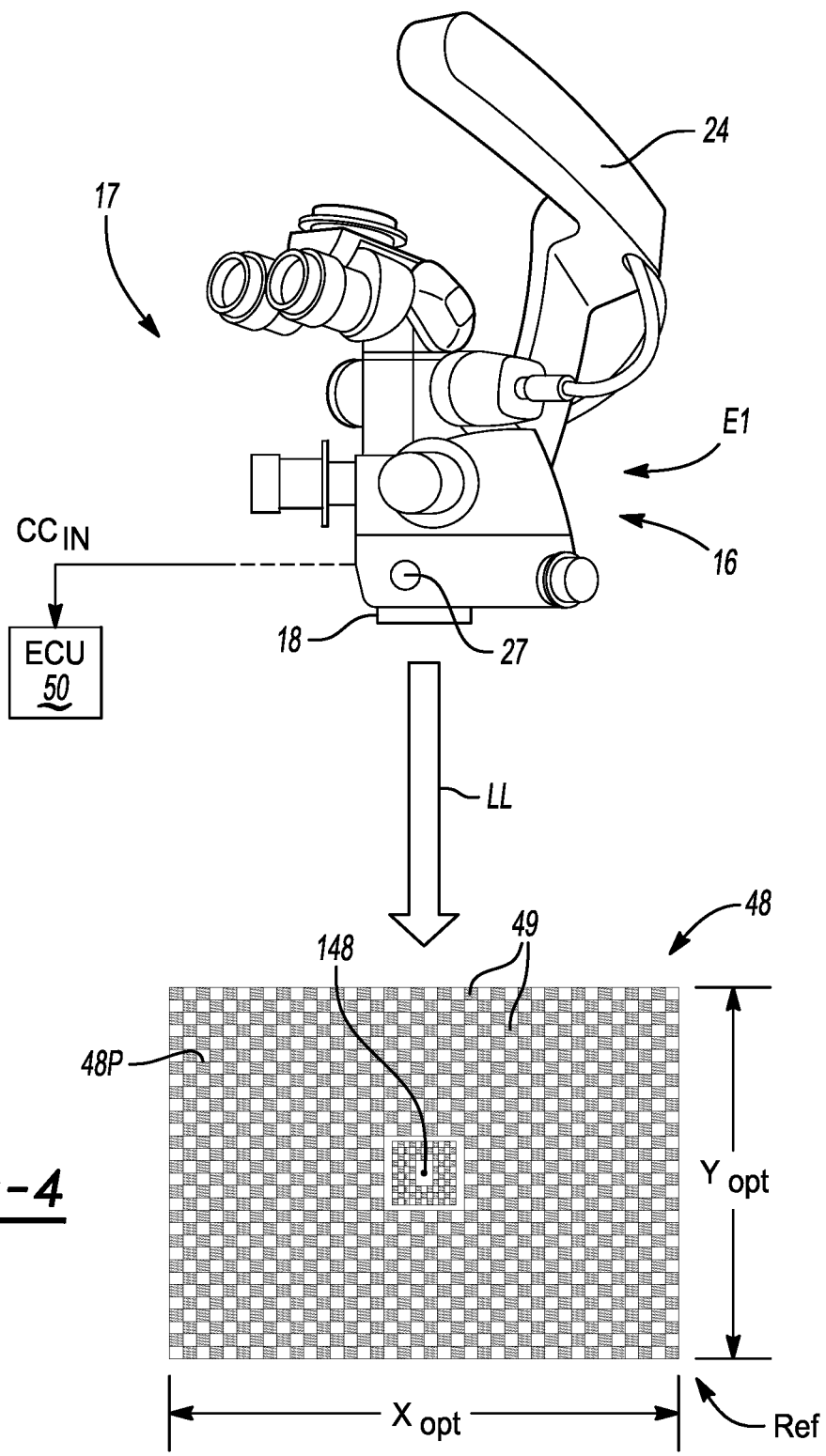
FIG. 4 is an illustration of a microscope-mounted digital camera arranged with respect to a checkerboard target when performing an embodiment of the method shown in FIG. 3.

Referring to FIG. 3 in conjunction with FIG. 4 depicting a microscope 17 inclusive of the digital camera 18, an embodiment of the above-summarized method, i.e., method 70, commences with block B72 ("Start"). The method 70 may be run for a given robotic camera system 14 to capture and correct for camera-specific variations. Block B72 is complete once the digital camera 18 has been securely mounted to the end-effector 26 situated at the distal end E1 of the serial robot 16. The method 70 then proceeds to block B74.

Block B74 ("Target Alignment") involves using the digital camera 18 to acquire an image of a reference target 48, with such an image referred to herein as a "reference image" for clarity. As shown in FIG. 4, the reference target 48 may be a pixelated target graphic 48P, e.g., a two-dimensional rectangular checkerboard image having alternate black and white pixels 49 having a y-axis dimension ($y_{OPT}$) and an x-axis dimension ($x_{OPT}$). During initial target alignment, the ECU 50 moves the serial robot 16 to default joint angles, and then attempts to rotate the serial robot 16 such that the x and y axes of the reference image are aligned with those of the reference target 48. The reference image need not be centered, as block B74 only aligns the x and y axes and saves the resulting joint angles to memory 54.

As part of block B74, the position of the focus motor 21 of FIG. 1 is initialized at a calibrated focal length. The calibrated focal length represents the focal length at which the ECU 50 will subsequently perform blocks B76, B78, and B80. For instance, the ECU 50 may set the focal length to 50% of a default quadratic working distance curve, itself stored in memory 54, or about 0.35 m to 0.45 m in a possible embodiment. Thus, block B74 entails receiving input signals (arrow $CC_{IN}$) via the ECU 50, itself in communication with the serial robot 16 of FIG. 1, with the input signals (arrow $CC_{IN}$) including a depth measurement, possibly measured using a depth sensor 27 as shown in FIG. 4 or derived from an auto-focus setting of the digital camera 18. The depth measurement is indicative of a linear distance along the optical axis (LL) of the digital camera 18 to the target object 19, with the digital camera 18 shown in a possible embodiment as integral with the microscope 17, e.g., an ophthalmic microscope. The input signals (arrow $CC_{IN}$) also include the joint position signals (arrow $CC_{30}$ of FIG. 1) indicative of a position of the distal end E1 of the serial robot 16 within the robot frame 25 (see FIGS. 1 and 2). The method 70 then proceeds to block B76.

At block B76 ("Angular Offsets"), the ECU 50 next determines roll and pitch offsets of a reference point within the above-noted reference image, doing so with respect to the robot frame 25. The roll and pitch offsets may be determined by moving the end-effector 26 of the serial robot 16 up or down along the z-axis and observing and recording via the ECU 50 the distance which the x and y locations of the center image 148 of FIG. 4 drift from the initial conditions. For example, the ECU 50 may employ an arctangent (atan) calculation to calculate the roll and pitch angles independently on the x and y axes, using a different or delta between the reference image and the measured displacement. The latter measurements may be achieved via the above-noted LTT logic, as will be appreciated by those skilled in the art. The ECU 50 may selectively perform several iterations of block B76 in order to refine accuracy, e.g., by iterating over roll and pitch parameters in a window of ±0.5 degrees.

Block B78 ("X,Y Offsets") may entail rotating the digital camera 18 about its z-axis. When this occurs, any x and y offsets at the Center of Projection (CoP) will cause the reference image to sweep out a circle trace. Thus, an Ax=b matrix may be used by the ECU 50 by calculating the delta in the x and y directions, as measured on the reference image, thereby allowing the ECU 50 to calculate the starting x and y positions. Block B78 therefor includes determining, via the ECU 50, an x-axis offset and a y-axis offset of the reference point with respect to the robot frame 25. The ECU 50 then stores x-axis offset and the y-axis offsets along with the roll and pitch offsets in the transformation matrix 75 of FIG. 1, within memory 54 of the ECU 50 or in another accessible location.

Figure 5:
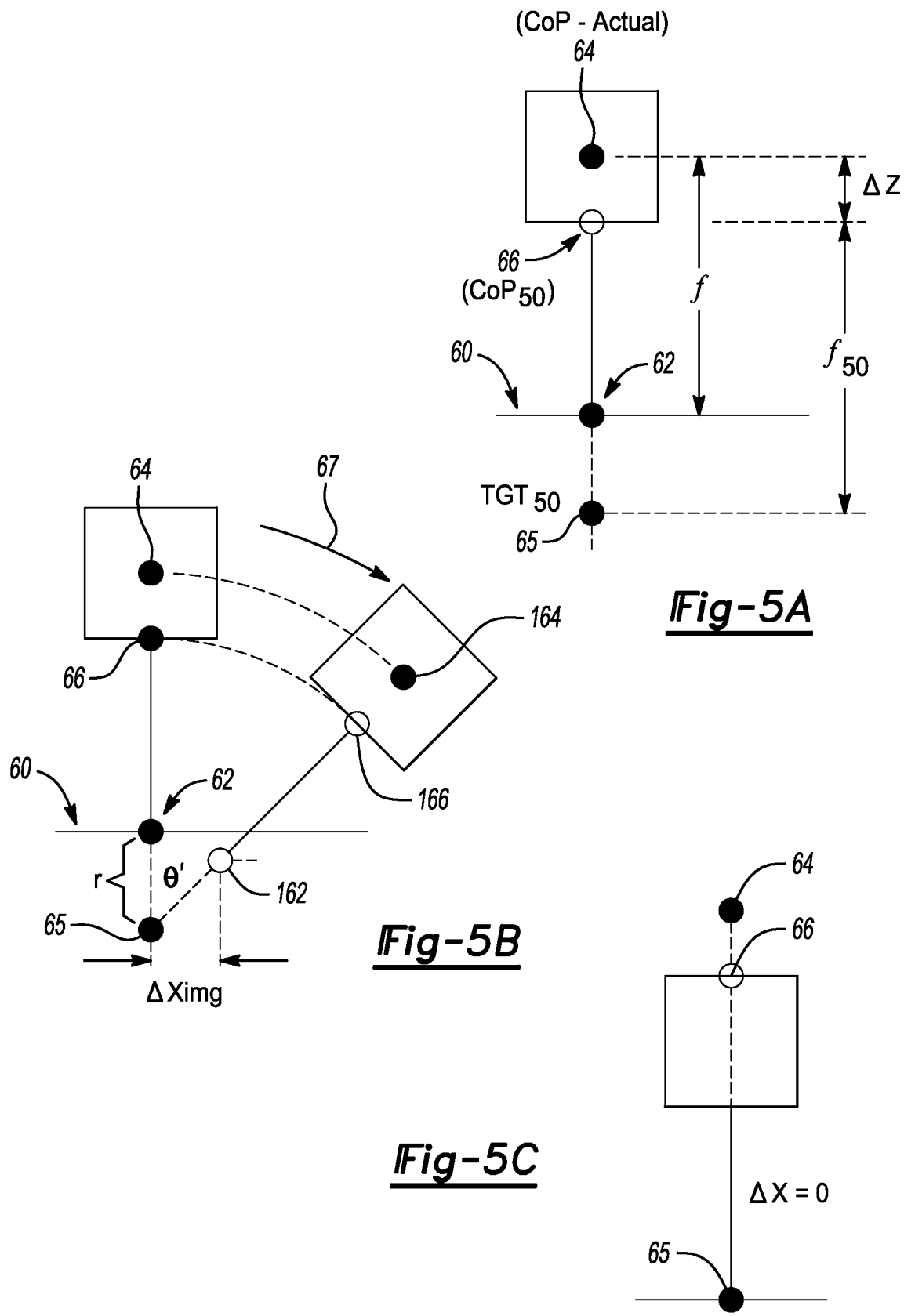
FIGS. 5A, 5B, and 5C are schematic illustrations of representative motion of a digital camera in the course of calibrating the optical axis thereof in accordance with an aspect of the subject disclosure.

Block B80 entails determining a z-axis offset after adjusting for the x and y offsets of block B78. Referring briefly to FIGS. 5A and 5B, the z-axis offset is one of the possible solutions of [f, z] to align the correct target z-axis location for a given focal length (f). The actual CoP is represented by point 64. Along the optical axis, a reference point 62 exists where the optical axis intersects the image plane 60. However, the ECU 50 may operate, prior to calibration using the method 70, with the erroneous understanding that the CoP is actually located at point 66 ($CoP_{50}$), and that the true position of the target is point 65 ($TGT_{50}$). Thus, the actual focal length (f) between points 64 and 62 differs from the focal length estimate ($f_{50}$) of the ECU 50, with the amount of the difference along the z-axis represented by $\Delta z$.

For block B80, the ECU 50 may run an experiment in which the serial robot 16 moves the digital camera 18 in a spherical range of motion by a known angle ($\theta'$), as represented by arrow 67 in FIG. 5B. The new corresponding positions of points 62, 64, and 66 are depicted in FIG. 5B as points 162, 164, and 166, respectively. Several such moves may be performed in a sequence, and an averaged delta may be used in the subsequent equations. A measurement error ($\Delta x_{img}$) thus results in the image plane.

Figure 6:
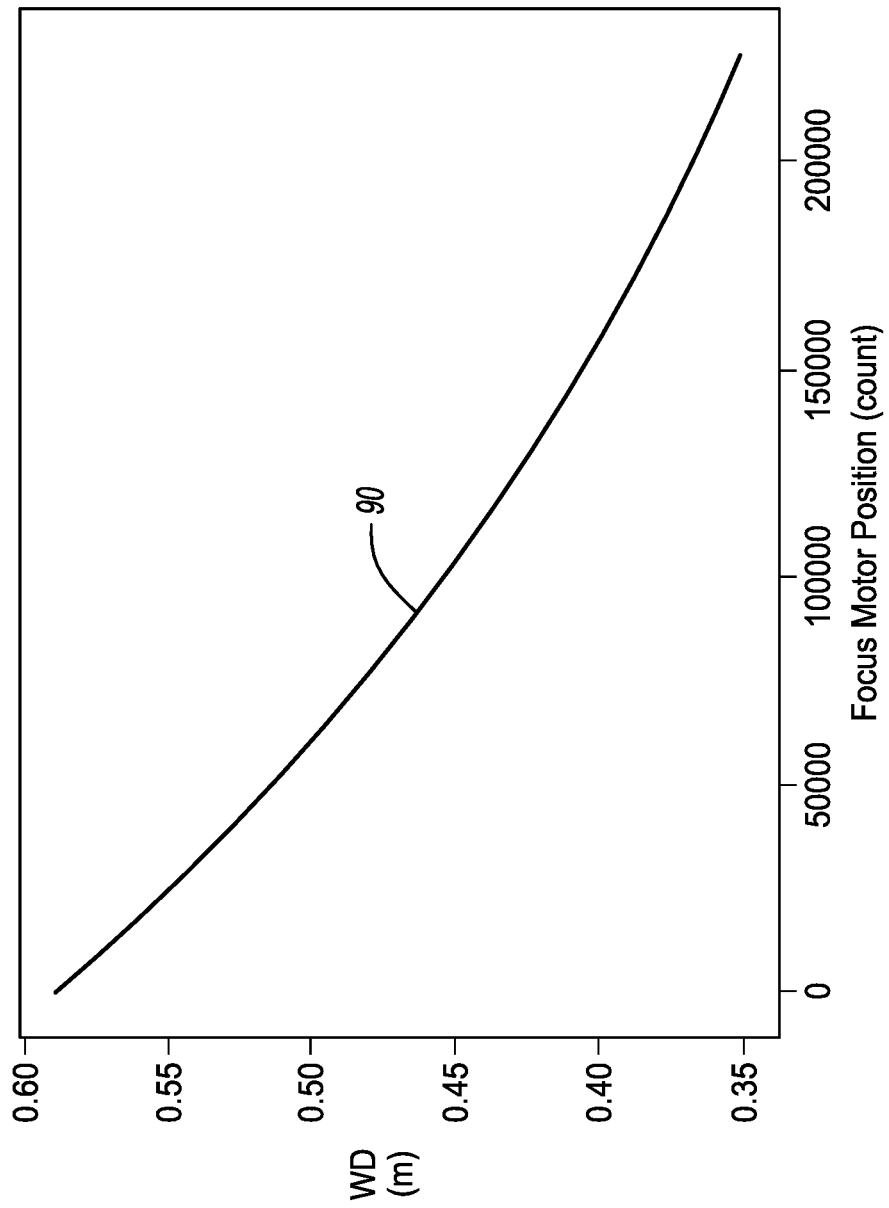
FIG. 6 is a graph of optical working distance versus focus motor position, with optical working distance represented in meters and depicted on the vertical axis, and with focus motor position represented in encoder counts and depicted on the horizontal axis.

A z-axis solution as depicted in FIG. 6 is to measure $x_{img}$, and to calculate the z-axis distance (r) using the known angle ($\theta'$). The ECU 50 can then shift the target point 65 up by the distance r) as follows:

$$\frac{\Delta x}{\sin(\theta)} = r$$

such that $\Delta x=0$ in the robot frame 25. Since the ECU 50 earlier in the method 70 locked in the calibrated focal length, an optimal solution is to simply set the z-axis offset used by the ECU 50 to be equal to the distance (r), which may be measured via the ECU 50 as understood in the art. The method 70 then proceeds to block B82.

Block B82 of the method 70 shown in FIG. 3 may entail creating a Focus-to-Optical Working Distance (F-to-WD) table in memory 54 of the ECU 50. This action may be accomplished offline, with values extracted from the table used during a subsequent operation of the robotic camera system 14 after adjusting for the above-described roll, pitch, and x, y, x axes offsets. For example, the ECU 50 may initialize at the calibrated focal length and thereafter populate the table. In a possible embodiment, the serial robot 16 moves the digital camera 18 along the view vector 100 of FIG. 2 by calibrated amounts toward each limit, at the direction of the ECU 50 or other suitable processing and control hardware, and then stores corresponding table entries of encoder positions or "counts", optical working distance (WD) in meters, in the lookup table. A curve 90 of such data shown in FIG. 8, with the curve 90 representing the corresponding z-axis offset for a given optical working distance (WD). That is, the ECU 50 uses the count-based position of the focus motor 21 (see FIG. 1) and the corresponding optical working distance (WD) to generate the illustrated curve 90.

When locking on to a target object 19 to perform a given LTT maneuver, the robot arm 24 of FIG. 1 is provided with the distance along the view vector 100 from the CoP to the target location. This value may be obtained by inputting the raw encoder position of the focus motor 21. Thus, a key end result of the present calibration method 70 is that position error is minimized using the transformation matrix 75 when calculating the location of the target object 19. In a practical sense, each time the ECU 50 enters LTT mode, the ECU 50 calculates the location of a corresponding LTT control frame, and asks the digital camera 18 to go through the optical working distance table, e.g., curve 90 of FIG. 8, in order to find the optical working distance (WD). The ECU 50 then creates the view vector 100. The terminating point of the view vector 100 is the target location, the position error of which is ultimately minimizing by execution of the method 70. If one were to consider a single optical working distance (WD), such as would be the case with a fixed optical working distance microscope 17, the ECU 50 would still determine a single z-axis offset so as to minimize error at that particular optical working distance. The functional equivalent of such an approach, therefore, is the population of a lookup table or memory location having single z-offset entry.

The method 70 of FIG. 3 then continues to block B84, where the ECU 50 uses the transformation matrix 75 of FIG. 1 to a control motion sequence of the serial robot 16 during a subsequent operation of the robotic camera system 14. Thus, when moving the serial robot 16 in response to commands from the ECU 50, e.g., autonomously generated or commanded by the surgeon, motion control logic of the ECU 50 is aware of the response in the camera frame 125, i.e., on the image plane, of incremental motion of the serial robot 16 in the robot frame 25. A surgeon wishing to visualize a specific point on the target object 19, e.g., a point on a patient's cornea or lens during an eye surgery, is therefore provided with a high confidence level that the target point will appear precisely where expected on a displayed digital image.

As will be appreciated by those skilled in the art in view of the foregoing disclosure, the calibration process enabled by execution of method 70 or logical variations thereof is intended to correct for slight variations between an expected alignment of the robot frame 25 and the camera frame 125. Whether due to a surgeon's adjustments to the view vector, tolerances in attaching the digital camera 18 to the end-effector 26 of FIG. 1, or other factors, a given camera might not perfectly coincide with an expected alignment in a given surgical suite 10. Thus, the described calibration effort is performed for a given camera-robot connection. Once the calibration steps of the method 70 have been completed, the method 70 can proceed to block B84, where a surgeon or clinician can enjoy the benefits of minimized position error during subsequent operation of the robot camera system 14. These and other potential benefits will be readily appreciated by those skilled in the art in view of the foregoing disclosure.

The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed:

1. A method for calibrating a robotic camera system having a digital camera that is integral with an ophthalmic microscope and connected to an end-effector of a serial robot, wherein the end-effector and the digital camera move within a robot motion coordinate frame, the method comprising:
    acquiring, using the digital camera, a reference image of a target object in an image plane having an optical coordinate frame, the target object including an eye of a human patient;
    receiving input signals via an electronic control unit (ECU) in communication with the serial robot and the digital camera, the input signals including a depth measurement indicative of a linear distance between the digital camera and the target object, and a set of joint position signals collectively describing a position of the digital camera within the robot motion coordinate frame, the robot motion coordinate frame having an x-axis, a y-axis, and a z-axis;
    determining, via the ECU, a roll offset and a pitch offset of a target point within the reference image with respect to the robot motion coordinate frame while moving the serial robot through a first calibrated motion sequence;
    determining, via the ECU after determining the roll offset and the pitch offset, each of an x-axis offset, a y-axis offset, and a z-axis offset of the target point with respect to the robot motion coordinate frame while moving the serial robot through a second calibrated motion sequence;
    storing the roll offset, the pitch offset, the x-axis offset, the y-axis offset, and the z-axis offset in a transformation matrix within memory of the ECU; and
    controlling a third motion sequence of the serial robot, via the ECU, during a subsequent operation of the robotic camera system using the transformation matrix, the subsequent operation of the robotic camera system being performed using the ophthalmic microscope as part of an eye surgery of the eye of the human patient.

2. The method of claim 1, wherein the digital camera has a variable optical working distance between the digital camera and the target object controlled by a focus motor, wherein determining the z-axis offset includes extracting the z-axis offset from a lookup table indexed by the variable optical working distance and a rotary position or encoder count of the focus motor.

3. The method of claim 2, further comprising:
    populating the lookup table via the ECU while controlling the focus motor through a focal range corresponding to the variable optical working distance.

4. The method of claim 1, further comprising:
    receiving an autofocus setting of the digital camera via the ECU; and
    processing the autofocus setting of the robotic camera system via the ECU to determine the depth measurement.

5. The method of claim 1, further comprising:
    measuring the depth measurement using a depth sensor; and
    measuring the joint position signals via a corresponding set of joint position sensors of the serial robot.

6. The method of claim 5, wherein measuring the depth measurement using a depth sensor is performed using a laser distance meter or an optical sensor.

7. The method of claim 1, wherein acquiring the reference image of the target object includes collecting a digital image of a two-dimensional checkerboard graphic using the digital camera.

8. The method of claim 1, further comprising:
    displaying three-dimensional images of the target object via one or more display screens during the subsequent operation.

9. A robotic camera system comprising:
    an ophthalmic microscope that is integral with a digital camera and connectable to an end-effector of a serial robot, wherein the end-effector and digital camera move within a robot motion coordinate frame; and
    an electronic control unit (ECU) in communication with the digital camera, and configured to:
        acquire, using the digital camera, a reference image of a target object in an image plane having an optical coordinate frame, the target object including an eye of a human patient;
        receive input signals, including a depth measurement indicative of a linear distance between the digital camera and the target object, and a set of joint position signals collectively describing a position of the digital camera in the robot motion coordinate frame, the robot motion coordinate frame having an x-axis, a y-axis, and a z-axis;
        determine a roll offset and a pitch offset of a target point within the reference image with respect to the robot motion coordinate frame while moving the serial robot through a first calibrated motion sequence;
        determine, after determining the roll offset and the pitch offset, each of an x-axis offset, a y-axis offset, and a z-axis offset of the target point with respect to the robot motion coordinate frame while moving the serial robot through a second calibrated motion sequence;
        store the roll offset, the pitch offset, the x-axis offset, the y-axis offset, and the z-axis offset in a transformation matrix within memory of the ECU; and
        control a third motion sequence of the serial robot using the transformation matrix during a subsequent operation of the robotic camera system, wherein the subsequent operation of the robotic camera system is performed using the ophthalmic microscope as part of an eye surgery of the eye of the human patient.

10. The robotic camera system of claim 9, further comprising the serial robot.

11. The robotic camera system of claim 9, wherein the digital camera includes a focus motor, and has a variable optical working distance between the digital camera and the image plane that is controlled by the focus motor, wherein the ECU is configured to extract the z-axis offset from a lookup table indexed by the variable optical working distance and a rotary position or encoder count of the focus motor.

12. The robotic camera system of claim 11, wherein the ECU is configured to populate the lookup table while controlling the focus motor through a focal range corresponding to the variable optical working distance.

13. The robotic camera system of claim 9, wherein the ECU is configured to receive an autofocus setting of the digital camera, and to determine the depth measurement using the autofocus setting.

14. The robotic camera system of claim 9, further comprising a depth sensor operable for determining the depth measurement.

15. The robotic camera system of claim 9, wherein the ECU is configured to acquire the reference image of the target object by collecting a digital image of a two-dimensional checkerboard graphic using the digital camera.

16. The robotic camera system of claim 14, wherein the depth sensor includes a laser distance meter or an optical sensor.

17. The robotic camera system of claim 9, further comprising one or more display screens, wherein the ECU is configured to display three-dimensional images of the target object via the one or more display screens during the subsequent operation.

18. A non-transitory computer-readable medium on which is recorded instructions, execution of which by a processor causes the processor, when used with a robot camera system having a digital camera connected to an end-effector of a serial robot, to:
  acquire, from a digital camera, that is integral with an ophthalmic microscope, a reference image of a target object on an image plane having an optical coordinate frame, the target object including an eye of a human patient;
  receive input signals, including a depth measurement indicative of a linear distance between the digital camera and the target object, and a set of joint position signals collectively describing a position of the digital camera in a robot motion coordinate frame, the robot motion coordinate frame having an x-axis, a y-axis, and a z-axis;
  determine a roll offset and a pitch offset of a target point within the reference image with respect to the robot motion coordinate frame while moving the serial robot through a first calibrated motion sequence;
  determine, after determining the roll offset and the pitch offset, each of an x-axis offset, a y-axis offset, and a z-axis offset of the target point with respect to the robot motion coordinate frame while moving the serial robot through a second calibrated motion sequence;
  store the roll offset, the pitch offset, the x-axis offset, the y-axis offset, and the z-axis offset in a transformation matrix within the computer-readable medium, thereby calibrating a robotic camera system having the digital camera; and
  control a third motion sequence of the serial robot during a subsequent operation of the robotic camera system use the transformation matrix to control, wherein the subsequent operation of the robotic camera system is performed using the ophthalmic microscope as part of an eye surgery of the eye of the human patient.

19. The non-transitory computer-readable medium of claim 18, wherein the digital camera is a stereoscopic camera, and the execution of the instructions by the processor causes the processor to:
  display three-dimensional images of the target object via one or more display screens during the subsequent operation.

20. The non-transitory computer-readable medium of claim 18, wherein the digital camera has a variable optical working distance between the digital camera and the image plane that is controlled by a focus motor, and wherein execution of the instructions by the processor causes the processor to:
  determine a rotary position or encoder count the focus motor; and
  extract the z-axis offset from a lookup table populated by the z-axis offset and indexed by the variable optical working distance and the rotary position or encoder count of the focus motor.

* * * * *